United States Patent
Hill et al.

(10) Patent No.: US 9,211,240 B2
(45) Date of Patent: Dec. 15, 2015

(54) MULTICOMPONENT ORAL CARE COMPOSITION

(71) Applicant: PERIPRODUCTS LTD, Middlesex (GB)

(72) Inventors: Robert Hill, Berkshire (GB); Alan J Collings, East Sussex (GB); Ian Baynes, Hertfordshire (GB); David G Gillam, London (GB)

(73) Assignee: Periproducts LTD, Eastcote, Ruislip, Middx (GB)

( * ) Notice: Subject to any disclaimer, the term of this patent is extended or adjusted under 35 U.S.C. 154(b) by 0 days.

(21) Appl. No.: 14/378,045

(22) PCT Filed: Feb. 4, 2013

(86) PCT No.: PCT/GB2013/050250
§ 371 (c)(1),
(2) Date: Aug. 11, 2014

(87) PCT Pub. No.: WO2013/117913
PCT Pub. Date: Aug. 15, 2013

(65) Prior Publication Data
US 2015/0017107 A1    Jan. 15, 2015

(30) Foreign Application Priority Data
Feb. 10, 2012 (GB) .................................. 1202341.2

(51) Int. Cl.
| | | |
|---|---|---|
| *A61K 8/24* | (2006.01) | |
| *A61K 8/20* | (2006.01) | |
| *A61K 8/21* | (2006.01) | |
| *A61Q 11/00* | (2006.01) | |
| *A61K 33/06* | (2006.01) | |
| *A61K 33/16* | (2006.01) | |
| *A61K 33/20* | (2006.01) | |
| *A61K 33/42* | (2006.01) | |

(52) U.S. Cl.
CPC ... *A61K 8/24* (2013.01); *A61K 8/20* (2013.01); *A61K 8/21* (2013.01); *A61K 33/06* (2013.01); *A61K 33/16* (2013.01); *A61K 33/20* (2013.01); *A61K 33/42* (2013.01); *A61Q 11/00* (2013.01); *A61K 2800/5922* (2013.01); *A61K 2800/92* (2013.01)

(58) Field of Classification Search
USPC ....................................................... 424/53
See application file for complete search history.

(56) References Cited

U.S. PATENT DOCUMENTS

| | | |
|---|---|---|
| 4,545,525 A | 10/1985 | Sachar et al. |
| 4,566,636 A | 1/1986 | Sachar et al. |
| 4,689,215 A | 8/1987 | Ratcliff |
| 4,696,811 A | 9/1987 | Ratcliff |
| 4,786,492 A | 11/1988 | Ratcliff |
| 4,788,053 A | 11/1988 | Ratcliff |
| 4,792,442 A | 12/1988 | Ratcliff |
| 4,793,989 A | 12/1988 | Ratcliff |
| 4,808,389 A | 2/1989 | Ratcliff |
| 4,818,519 A | 4/1989 | Ratcliff |
| 4,837,009 A | 6/1989 | Ratcliff |
| 4,851,213 A | 7/1989 | Ratcliff |
| 4,855,135 A | 8/1989 | Ratcliff |
| 4,886,657 A | 12/1989 | Ratcliff |
| 4,889,714 A | 12/1989 | Ratcliff |
| 4,925,656 A | 5/1990 | Ratcliff |
| 4,975,285 A | 12/1990 | Ratcliff |
| 5,052,590 A | 10/1991 | Ratcliff |
| 5,112,479 A | 5/1992 | Srimongkolkul |
| 5,200,171 A | 4/1993 | Ratcliff |
| 5,348,734 A | 9/1994 | Ratcliff |
| 5,489,435 A | 2/1996 | Ratcliff |
| 5,618,550 A | 4/1997 | Ratcliff |
| 5,811,115 A | 9/1998 | Ratcliff |
| 5,834,003 A | 11/1998 | Ratcliff |
| 5,902,575 A | 5/1999 | Ratcliff |
| 5,935,592 A | 8/1999 | Ratcliff |
| 6,017,554 A | 1/2000 | Ratcliff |
| 6,030,391 A | 2/2000 | Brainard et al. |
| 6,114,398 A | 9/2000 | Ratcliff |

(Continued)

FOREIGN PATENT DOCUMENTS

| | | | |
|---|---|---|---|
| AU | 4953585 A | | 4/1987 |
| AU | 642128 B2 | | 10/1993 |

(Continued)

OTHER PUBLICATIONS

International Search Report for PCT/GB2013/050250, mailed May 9, 2014.

(Continued)

*Primary Examiner* — Walter Webb
(74) *Attorney, Agent, or Firm* — Meunier Carlin & Curfman LLC

(57) ABSTRACT

The present invention relates to a multicomponent oral health care composition, comprising a source of a fluoride ion, a source of a calcium ion, a source of a phosphate ion, and stabilized chlorine dioxide, that can be used as a toothpaste, oral spray or a mouth wash/oral rinse formulation. The different components in the composition act synergistically together to clean the teeth and mucous membranes of an oral cavity of a subject, perfuming them or protecting them in order to keep them in good condition, change their appearance or correct unpleasant odors. They achieve this by inhibiting caries, promoting teeth remineralization, and helping to alleviate dentine hypersensitivity, gingivitis and periodontal disease.

22 Claims, 14 Drawing Sheets

(56) References Cited

U.S. PATENT DOCUMENTS

| | | |
|---|---|---|
| 6,136,348 A | 10/2000 | Ratcliff et al. |
| 6,200,557 B1 | 3/2001 | Ratcliff |
| 6,208,881 B1 | 3/2001 | Champeau |
| 6,274,132 B1 | 8/2001 | Ratcliff |
| 6,277,363 B1 | 8/2001 | Ratcliff |
| 6,280,716 B1 | 8/2001 | Ratcliff |
| 6,287,551 B1 | 9/2001 | Ratcliff |
| 6,878,373 B2 | 4/2005 | Keeton et al. |
| 2002/0197215 A1 | 12/2002 | Stier |
| 2005/0260269 A1 | 11/2005 | Engelbrecht et al. |
| 2006/0134020 A1 | 6/2006 | Robinson et al. |
| 2008/0292565 A1 | 11/2008 | Tung |
| 2009/0016973 A1 | 1/2009 | Ratcliff et al. |
| 2009/0317339 A1* | 12/2009 | Sharma et al. ........... 424/49 |
| 2010/0074970 A1 | 3/2010 | Ratcliff et al. |
| 2011/0318282 A1 | 12/2011 | Ratcliff et al. |
| 2014/0112875 A1 | 4/2014 | Ratcliff et al. |

FOREIGN PATENT DOCUMENTS

| | | |
|---|---|---|
| CA | 999238 A2 | 1/1973 |
| CA | 2090154 A1 | 8/1994 |
| CA | 1336507 C | 8/1995 |
| CA | 2474113 A1 | 1/2006 |
| CA | 2623769 A1 | 1/2009 |
| CA | 2624125 A1 | 1/2009 |
| CA | 2794242 A1 | 9/2011 |
| DE | 2134862 A1 | 1/1973 |
| DE | 3855561 T2 | 2/1997 |
| DE | 69315324 T2 | 5/1998 |
| EP | 0342746 A1 | 11/1989 |
| EP | 0431672 A1 | 6/1991 |
| EP | 0461105 A1 | 12/1991 |
| EP | 0613678 A1 | 9/1994 |
| EP | 1094513 A2 | 4/2001 |
| EP | 1736135 A1 | 12/2006 |
| GB | 2275607 A | 9/1994 |
| GB | 2478478 B | 5/2013 |
| IT | 1208577 B | 7/1989 |
| MX | 2011006781 A | 12/2011 |
| WO | 8701969 A1 | 4/1987 |
| WO | 0003747 A2 | 1/2000 |
| WO | 03047353 A1 | 6/2003 |
| WO | 2005097053 A1 | 10/2005 |
| WO | 2006108432 A1 | 10/2006 |
| WO | 2007065856 A1 | 6/2007 |
| WO | 2007066837 A1 | 6/2007 |
| WO | 2007090242 A1 | 8/2007 |
| WO | 2010075419 A1 | 7/2010 |
| WO | 2011094872 A1 | 8/2011 |
| WO | 2011099991 A1 | 8/2011 |
| WO | 2011119177 A1 | 9/2011 |
| WO | 2012087374 A1 | 6/2012 |

OTHER PUBLICATIONS

Office Action for GB1202341, mailed Jun. 1, 2012.
Office Action for GB1301794, mailed Oct. 11, 2013.
Office Action for GB1301794, mailed May 29, 2013.
Written Opinion of the International Preliminary Examining Authority for PCT/GB2013/050250, dated Sep. 25, 2014.
Written Opinion of the International Searching Authority for PCT/GB2013/050250, dated Aug. 10, 2014.
International Preliminary Report on Patentability Chapter II for PCT/GB2013/050250, dated Jan. 5, 2015.

* cited by examiner

MULTICOMPONENT ORAL CARE COMPOSITION

The present invention relates to a multicomponent oral health care composition that can be used as a toothpaste, oral spray or a mouth wash/oral rinse formulation. The different components in the composition act synergistically together to clean the teeth and mucous membranes of an oral cavity of a subject, perfuming them or protecting them in order to keep them in good condition, change their appearance or correct unpleasant odours. They achieve this by inhibiting caries, promoting teeth remineralisation, and helping to alleviate dentine hypersensitivity, gingivitis and periodontal disease.

Tooth mineral in humans and animals is based on calcium apatite, $Ca_5(PO_4)_3OH$. Natural tooth apatites are heavily solid substituted, and the $Ca^{2+}$ cations in the crystal lattice may be replaced by, for example, $Sr^{2+}$, $Mg^{2+}$ or $Zn^{2+}$, or by two $Na^+$ cations. The phosphate $(PO_4)^{3-}$ anions may be replaced by carbonate ions $(CO_3^{2-})$, with an associated $Na^+$ cation replacing a $Ca^{2+}$ cation or the associated loss of a hydroxyl ion $(OH^-)$. The hydroxyl ion may also be replaced by a fluoride ion $(F^-)$. This latter substitution occurs readily in tooth enamel and has several beneficial effects. In the crystal structure of calcium apatite, the hydroxyl ion is displaced slightly above the plane of a triangle of Ca(II) ions (as depicted in FIG. 3), whilst the smaller fluoride ion sits in the centre of the Ca(II) triangle. This results in hydroxyapatite (HA) having a slightly distorted monoclinic crystal structure, whilst fluorapatite has a more symmetric hexagonal crystal structure. This difference leads to fluorapatite being:
  i) More stable to acid dissolution and more resistant to the acids produced by caries forming bacteria; and
  ii) Formed more readily, since fluorapatite has a lower solubility product than hydroxyapatite.

As a consequence of these two factors, soluble fluoride salts have been added to toothpastes, mouth rinses and drinking water for over fifty years, and fluoride has a well-documented and recognised role in anti-caries treatment. The use of fluoride as a preventive measure is well established.

It is generally recognised that plaque that forms on teeth as a result of the activity of bacteria is not completely removed by the act of brushing teeth. The plaque may act as a reservoir for fluoride in the mouth, where it is thought to form fluorite-like species, such as calcium fluoride $(CaF_2)$. The accumulation of dental plaque biofilms, whilst it may possibly be desirable as a fluoride reservoir, is also the source of the acid-producing bacteria that cause caries and gingivitis, which can progress to become periodontal disease. Their presence is therefore undesirable. However, fluoride becomes integrated within the hydroxyapatite crystals, creating enlarged and less soluble crystals. Because these crystals are less soluble and less reactive, as they are more stable to acid dissolution and more resistant to the acids produced by caries-forming bacteria, dissolution of tooth structure by acid by-products of microorganism metabolism cannot occur as readily. The action of fluoride on hydroxyapatite crystals therefore makes it an aid in the prevention or minimisation of dental caries and periodontal disease.

In contrast, free fluoride in saliva is rapidly diluted by salivary flow and exchange. Salivary flow rates vary enormously from individual to individual and vary during the course of the day, reducing almost to zero during sleep. Salivary flow rates are typically about 0.25 to 1.2 ml/min during the day, while the salivary volumes are typically about 1-10 ml. Additionally, salivary flow rates are observed to reduce with age and with smoking.

Fluoride uptake into enamel, and into incipient caries lesions and the resulting formation of fluorapatite, is retarded by the presence of plaque. The plaque acts as a barrier to fluoride uptake. In the absence of plaque, fluoride uptake into enamel is extremely rapid. It is important to note that remineralisation requires a source of both $Ca^{2+}$ and $PO_4^{3-}$ ions in addition to fluoride in order to form fluorapatite. Fluoride is proposed to enhance the precipitation of fluorapatite crystals in solutions containing calcium and phosphate and therefore tends to prevent the demineralisation of teeth. Evidence has linked fluorite to enhancing iron absorption. The calcium and phosphate may come from the saliva itself. However, particularly in individuals with low salivary flow rates, such as the elderly and smokers, or during night times when salivary flow rates are reduced, it is preferable to have an additional source of $F^-$, $Ca^{2+}$, and $PO_4^{3-}$ within the toothpaste itself. This may be provided by soluble forms of $F^-$, $Ca^{2+}$, and $PO_4^{3-}$, or more preferably particulate, sparingly soluble forms that give rise to controlled release of calcium and phosphate as a result of the particles adhering to the teeth and gingivae and slowly dissolving. Examples include bioactive glasses, and particularly hydroxyapatite.

Studies have demonstrated that oral gram-negative anaerobic bacteria and several species of other oral bacteria can produce volatile sulphur compounds (VSC), such as hydrogen sulphide methyl mercaptan and dimethyl sulphide. Malodorous VSC are generated primarily through the putrefactive action of oral microorganisms on sulphur-containing amino acids, peptones or proteins found in the oral cavity of a human or animal subject. These substrates are readily available in saliva and dental plaque, or may be derived from proteinaceous food particles, as well as exfoliated oral epithelium food debris.

Stabilised chlorine dioxide $(ClO_2)$ is an aqueous solution containing chlorite ions and stabilisers. The stabilisers may comprise, for example, a carbonate or bicarbonate buffering system. When the pH of stabilised chlorine dioxide falls below a neutral pH, the molecular chlorine dioxide radical is released. The chlorine dioxide has bacteriocidal and bacteriostatic effects on the bacteria in the oral cavity of a human or animal subject. Stabilised chlorine dioxide reacts with the cell walls of microorganisms (changing the proteins and fats in the cell wall membrane), acts as a strong oxidising agent (oxidising the polysaccharide matrix that keeps the biofilm together) and effectively kills pathogenic microorganisms such as fungi, bacteria and viruses.

Chlorine dioxide has a well proven role in destroying the bacteria involved in plaque formation, caries, gingivitis and periodontal disease, as well as eliminating halitosis. As chlorine dioxide destroys the plaque-forming bacteria, it is particularly effective in plaque removal, in conjunction with physical tooth brushing. Removal of this plaque will remove the physical barrier to fluoride, calcium and phosphate ions being able to reach the demineralised tooth surface, and thus promotes and enhances remineralisation of the tooth surface.

However, there is always a need and a desire in the technical field to provide oral care compositions which are more effective still in effecting the minimisation of the amount of plaque within the oral cavity and facilitating the remineralisation of teeth.

Therefore, in accordance with the present invention there is provided an oral care composition comprising:
  i) A source of a fluoride ion;
  ii) A source of a calcium ion;
  iii) A source of a phosphate ion; and
  iv) stabilised chlorine dioxide.

These components have, to date, never been employed together in a single oral care composition. The combination of the components is surprisingly able to exhibit a synergistic effect over and above the effects observed when using each component on an individual basis, or when using a composition which does not contain all of the components.

According to one embodiment of the invention, the source of a fluoride ion is typically a soluble fluoride salt. Exemplary sources of fluoride ions which are envisaged by the present invention include, but are not limited to, sodium fluoride, potassium fluoride, disodium monofluorophosphate, tin (II) fluoride (stannous fluoride), dipotassium fluorophosphates, calcium fluorophosphates, calcium fluoride, ammonium fluoride, aluminium fluoride, hexadecyl ammonium fluoride, 3-(N-hexadecyl-N-2-hydroxy-ethylammonio) ammonium difluoride, N,N',N'-Tris(polyoxyethylene)-N-hexadecyl-propylenediaminedihydrofluoride disodium hexafluoro silicate, dipotassiumhexafluorosilicate, ammonium hexafluorosilicate, magnesium hexafluorosilicate, or ammonium fluorophosphates, or any combinations of two or more thereof.

According to one embodiment, the source of fluoride ions has a concentration of fluoride between about 20 and about 1500 ppm as fluorine.

The source of fluoride ions may have a concentration in the range of between about 0.1% to about 3.0% (w/v) in the oral care composition, typically between about 0.25% to about 2.0% (w/v), more typically between about 0.50% to about 1.5% (w/v), still more typically between about 1.00% to about 1.2% (w/v).

According to another embodiment of the invention, both the calcium ions and the phosphate ions are typically provided by an apatite species, such as a nano-crystalline apatite. Nano-crystalline is defined herein as where the crystallites have a size of less than about 100 nm.

In the present invention, the crystallite sizes of the apatites are determined from X-ray diffraction line width data using the Scherrer Line broadening method. In this method, the width at half height of the 002 reflection $\beta_{002}$ is inversely proportional to crystallite length in the c-axis direction (Cullity 1956) and is given by the equation:

$$D = 0.9\lambda/(\beta_{002} \cos \theta)$$

Where D is the crystallite size in nm; $\lambda$ is the wavelength of the incident X-rays, 0.154 nm; $\beta_{002}$ is the width at half height of the 002 reflection and cos $\theta$ is the cosine of the X-ray incident angle (25.85°). The 002 reflection is a term well known to a person skilled in the art, and is explained in, for example, the textbook 'Elements of X-Ray Diffraction', (3rd Edition); B. D. Cullity (2001); Addison-Wesley Chapter 2; ISBN-10: 0201610914.

It is to be noted that this method neglects instrumental line broadening which is negligible for small nm sized crystals, and also neglects strain effects in the lattice and solid substitution effects.

It is the unique combination of fluoride, calcium, phosphate, and stabilised chlorine dioxide, in one single oral care composition, that is able to act synergistically together to inhibit caries, promote remineralisation of the teeth, and help with dentine hypersensitivity, gingivitis and periodontal disease.

According to one embodiment, the composition contains an appropriate buffering system. Exemplary buffer systems which are envisaged by the present invention include, but are not limited to, those comprising one or more of acetate, carbonate, citrate or phosphate salts.

The oral care composition may be contained within, for example, a toothpaste, oral spray or a mouth wash/oral rinse formulation, or in any other formulation which may be used for the improvement of oral hygiene. Such formulations will of course be readily apparent to a person skilled in the art.

The oral care composition of the invention is able to achieve remineralisation of incipient caries lesions much more effectively than when the components therein are utilised individually or separately. The fluoride source provides fluoride ions for forming fluorapatite, whilst the hydroxyapatite can provide both the calcium and phosphate ions, and the chlorine dioxide kills the bacteria forming the plaque. Use of this composition substantially eliminates the plaque and facilitates the uptake of $Ca^{2+}$, $PO_4^{3-}$ and $F^-$ ions into the tooth structure and enables remineralisation to occur. The effect of the composition is further enhanced when employed in combination with physical brushing of the teeth.

According to another embodiment, the apatite is based on the formula $M_5(PO_4)_3X$, wherein M may be Ca, Sr, Zn or Mg, and X may be F, Cl or OH. Specific apatite compounds used in accordance with the invention may therefore include, but are not limited to, substituted or unsubstituted hydroxyapatites, substituted or unsubstituted fluorapatites, or substituted or unsubstituted hydroxycarbonated apatites, such as calcium hydroxyapatite, strontium hydroxyapatite, calcium hydroxycarbonated apatite, strontium hydroxycarbonated apatite, calcium fluorapatite, strontium fluorapatite, mixed strontium/calcium apatites or a mixed hydroxyfluorapatite, zinc substituted hydroxyapatite, zinc carbonated hydroxyapatite, zinc fluorapatite, or octacalcium phosphate.

The stabilised chlorine dioxide solution may have a concentration in the range of between about 0.05% to about 2.0% (w/v) in the oral care composition, typically between about 0.075% to about 1.0% (w/v), more typically between about 0.10% to about 0.5% (w/v), still more typically between about 0.12% to about 0.2% (w/v), and/or may have a pH or be buffered to a pH of between about 6.0 and about 8.0, typically between about 7.0 and about 8.0.

When the composition is to be used as toothpaste formulation, the source of fluoride ions may have a fluoride ion concentration of between about 300 ppm and about 1500 ppm.

When the composition is to be used as mouth wash or oral rinse formulation, the source of fluoride ions may have an active fluoride ion concentration of between about 5 and about 500 ppm. By 'active' fluoride ion concentration is meant the amount of fluoride ion that is free and available for reaction and involvement in the remineralisation process. Depending upon the fluoride ion source used, this may be less than the total fluoride ion concentration in the overall oral composition.

Also provided in accordance with the present invention is the use of a stabilised chlorine dioxide solution in combination with a source of calcium ions, a source of phosphate ions and a source of fluoride ions, to generate gaseous chlorine dioxide within the oral cavity without the use of extra oral sources of acidification. The calcium ions and phosphate ions may be provided together by an apatite species as detailed hereinabove.

According to another embodiment, the apatite may be present in an amount of from about 0.5 to about 30 weight percent of the oral care composition. Alternatively, or in addition, the apatite may have a particle size distribution such that at least about 3% of the mass of the particles have a size less than about 5 microns and where the apatite has a crystallite size of less than about 200 nm.

According to another embodiment of the invention, the apatite may be present in an amount of from about 0.5 to about 25 weight percent of the composition. Alternatively, or in addition, the apatite particle size distribution may have at least about 15% of the mass of the particles below about 5 microns and where the apatite crystallite size is from about 30 to about 50 nm.

According to another embodiment, the apatite may be present from about 0.5 to about 15 weight percent of the composition. Alternatively, or in addition, at least about 50% of the mass of the particles may have a particle size less than about 5 microns.

The composition of the invention may also contain other components selected from one or more of a solvent, a thickening agent or viscosity modifier, an abrasive, a flavour, an aromatic component, a humectant, a sweetener, a carrier, a remineralising agent, a film forming agent, a buffering agent, a cooling agent, a pH adjusting agent, an oxidizing agent, and a colorant.

Exemplary such compounds which may be added to the composition of the invention may include, but are not limited to, glycerol, water, hydrated silica, cellulose gum, trisodium phosphate, sodium saccharin, mentha extracts, citric acid, limonene, linalool, and titanium dioxide.

According to one embodiment of the mouth wash or oral rinse formulation of the invention, this formulation may also comprise a linear polysaccharide polymer with a high yield value that exhibits pseudoplastic flow to stabilise the HA in suspension. Typically, a linear polysaccharide gum where one or more hydroxyl groups on the monosaccharide is substituted with a functional group that comprises a carboxyl group (R—COOH), an acyl group (RCO—) or a sulphate group (R—OSO$_3^-$) is used. Examples of such types of substituted polysaccharide include, but are not limited to, algin, xanthan gum, gellan gum and carrageenan.

Also provided in accordance with the present invention is the use of an oral care composition in the cleaning of teeth and mucous membranes of the oral cavity of a subject, perfuming them or protecting them in order to keep them in good condition, change their appearance or correct unpleasant odours.

A second aspect of the invention deals with dentine hypersensitivity. Dentine hypersensitivity is felt when nerves inside the dentin of the teeth are exposed, and results in pain associated with mechanical stimuli, such as that caused by the intake of hot or cold foodstuffs into the mouth. This typically affects more than 40% of the population. It is a result of fluid flow in exposed open dentinal tubules that results in pressure changes that trigger nerve transmission within the pulp chamber of a tooth. Dentinal tubules become exposed as a result of three causes:

i) Gingival recession where the gums recede exposing the dentine;

ii) Loss of the enamel as a result of caries or acid erosion; or iii) Loss of the enamel as a result of abrasive wear accompanying tooth brushing.

Treatment generally involves sealing or blocking the dentinal tubules. This is often achieved using specialised toothpastes that are designed to occlude the dentinal tubules. The dentinal tubule openings are typically about 2-5 microns in diameter.

One way these tubules can be blocked is to precipitate a material onto the surface over the top of the tubules. Another approach, i.e. that used by the present invention, is to have particles comparable in size to the openings of the dentinal tubules, so the particles are able to enter into the tubules and occlude them. It is important that there are sufficient particles of the required size present to give effective numbers penetrating the dental tubules.

Also provided in accordance with the present invention is an oral care composition as defined herein above in the remineralisation of teeth or in the treatment of dentine hypersensitivity.

According to a further embodiment of the invention, there is provided a method of cleaning teeth and mucous membranes of the oral cavity of a subject, or perfuming them or protecting them in order to keep them in good condition, comprising applying an oral care composition as defined hereinabove.

According to another embodiment, the apatite may be present in an amount of from about 0.5 to about 30 weight percent of the oral care composition. Alternatively, or in addition, the apatite may have a particle size distribution such that at least about 3% of the mass of the particles have a size less than about 5 microns and where the apatite has a crystallite size of less than about 200 nm.

According to another embodiment of the invention, the apatite may be present in an amount of from about 0.5 to about 25 weight percent of the composition. Alternatively, or in addition, the apatite particle size distribution may have at least about 15% of the mass of the particles below about 5 microns and where the apatite crystallite size is from about 30 to about 50 nm.

According to another embodiment, the apatite may be present from about 0.5 to about 15 weight percent of the composition. Alternatively, or in addition, at least about 50% of the mass of the particles may have a particle size less than about 5 microns.

Also provided by the present invention is a toothpaste comprising an oral care composition of the invention as defined hereinabove. The apatite species in the toothpaste, such as a nano-crystalline hydroxyapatite, comprises small crystallites having a size of less than about 100 nm and a large surface area to facilitate dissolution. However, the larger particles which can occlude the dentinal tubules comprise many hundreds of crystallites aggregated together to form an approximately spherical particle with dimensions in the range 0.1 to 5 microns, and thus are similar in size to the openings to the dentinal tubules.

Table 1 summarises the particle size data from a range of nano-crystalline hydroxyapatites in terms of the D10, D50 and D90 values which represent the volume fractions below the specified values. It can be seen from the particle sizes in the Table that they are of a similar size to the openings to the dentinal tubules, and are therefore able to occlude dentinal tubules.

TABLE 1

| Hydroxyapatite Samples | X-ray results | FTIR | Particle Size D10/D50/D90 (microns) |
|---|---|---|---|
| A | Nanocrystalline Hydroxyapatite | Minimal $CO_3^{2-}$ content | 1.20/4.16/11.40 |
| B | Nanocrystalline Hydroxyapatite | Minimal $CO_3^{2-}$ content | 1.19 3.78/11.15 |
| C | Nanocrystalline Hydroxycarbonate | Minimal $CO_3^{2-}$ content content | 0.32/2.50/22.58 Broad Particle Size |
| D | Pure Hydroxyapatite No Nanocrystallinity | No $CO_3^{2-}$ | 0.25/1.29/8.71 |
| E | Pure Hydroxyapatite No Nanocrystallinity | Minimal $CO_3^{2-}$ content | 1.20/3.35/6.32 |
| F | Nano Hydroxyapatite | Minimal $CO_3^{2-}$ content | 1.57/4.47/10.14 |

All carbonate contents were <1%, and are so low they are not quantifiable. The carbonate detected is purely derived from atmospheric contamination during synthesis.

The invention will now be described further by way of example with reference to the following Figures which are intended to be illustrative only and in no way limiting upon the scope of the invention.

Figure 1:
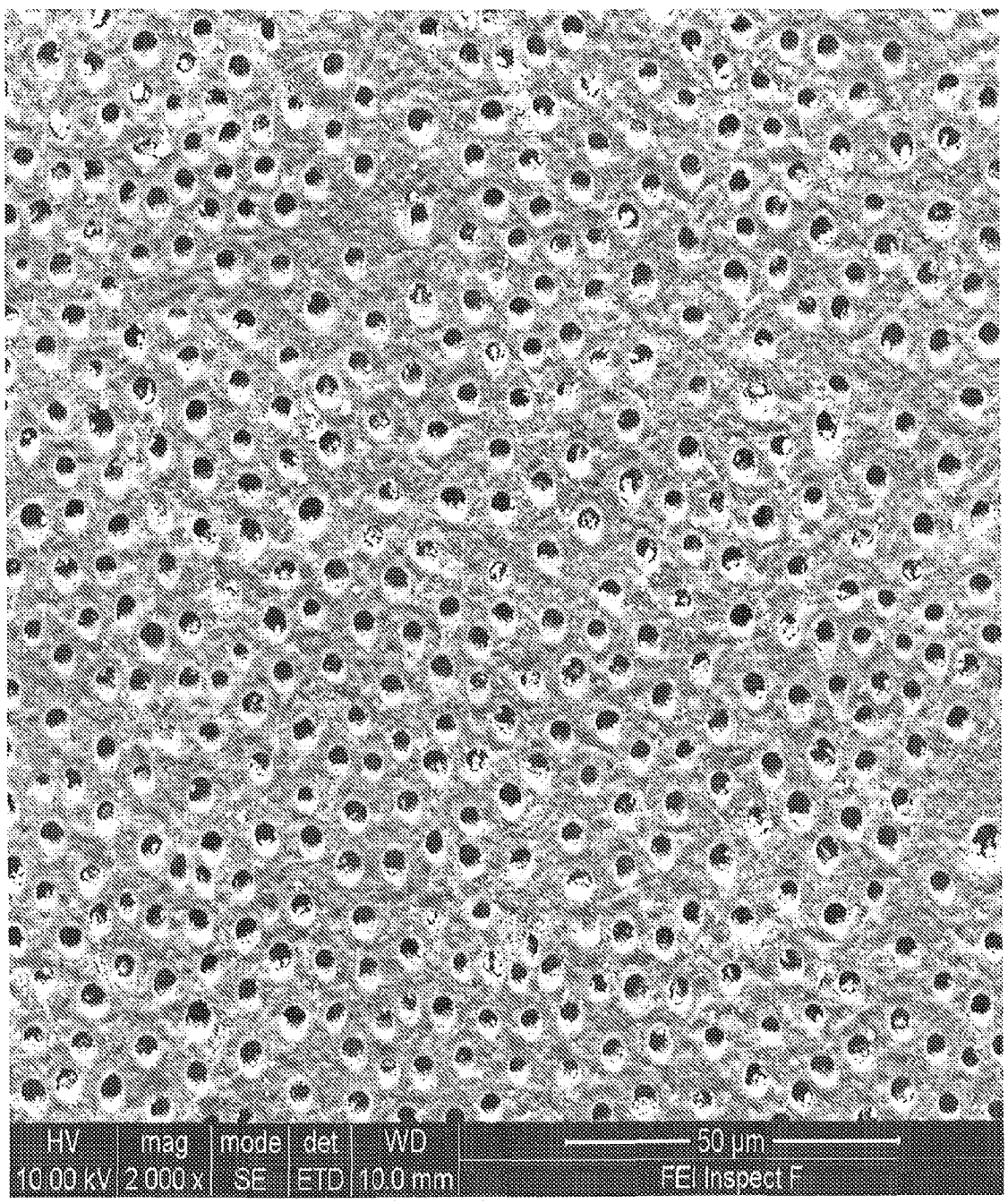
FIG. 1 shows a scanning electron micrograph of open dentinal tubules.
Figure 2:
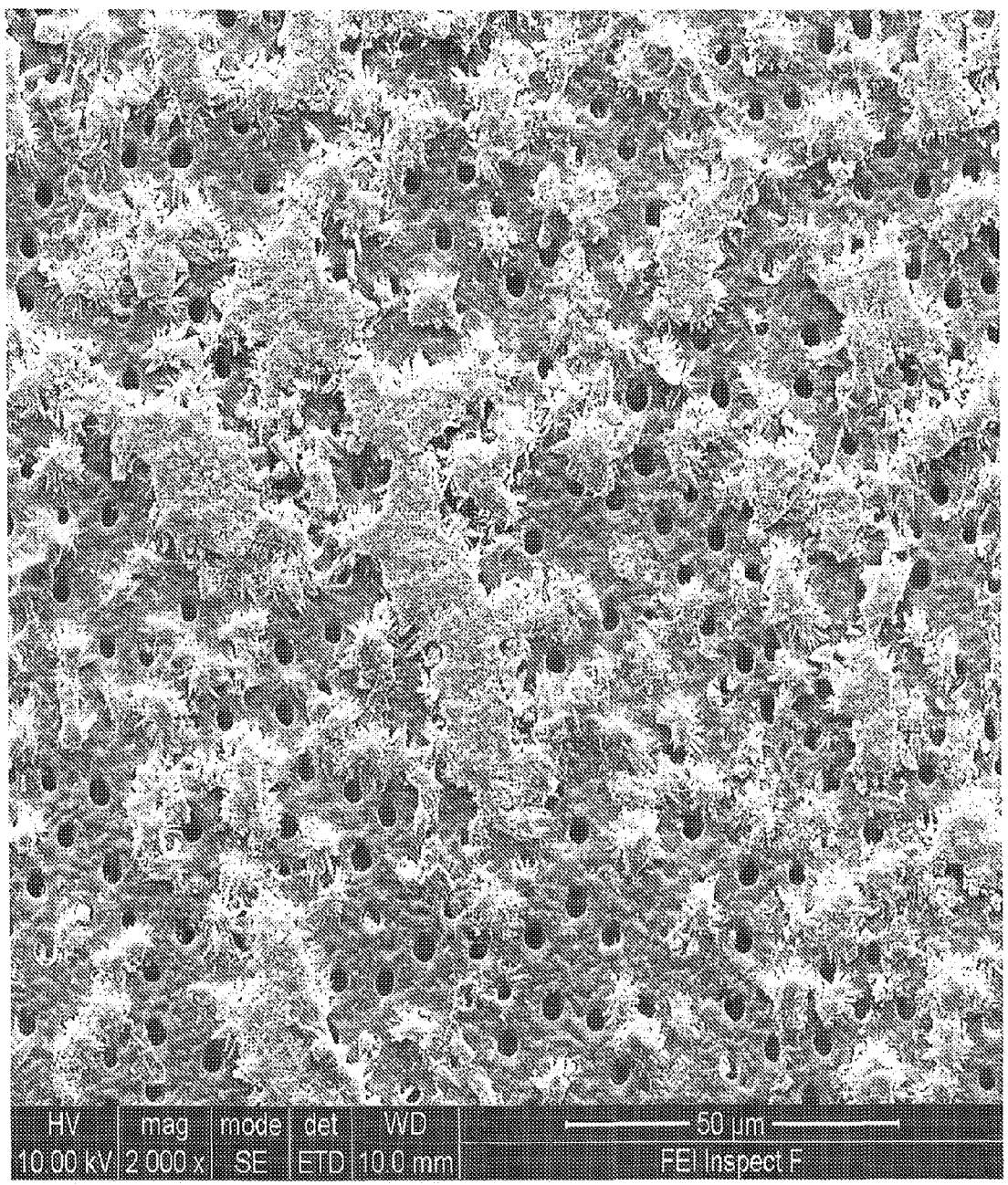
FIG. 2 shows a scanning electron micrograph of dentinal tubules being blocked by precipitate of a material over the top of the tubules.

FIG. 1 shows a scanning electron micrograph of open dentinal tubules. One way these tubules can be blocked is to precipitate a material onto the surface over the top of the tubules. This is shown in FIG. 2, which depicts a material (in this instance, Colgate ProRelief) over the top of the tubules. As can be seen, not many of the openings of the tubules are blocked.

Figure 3:
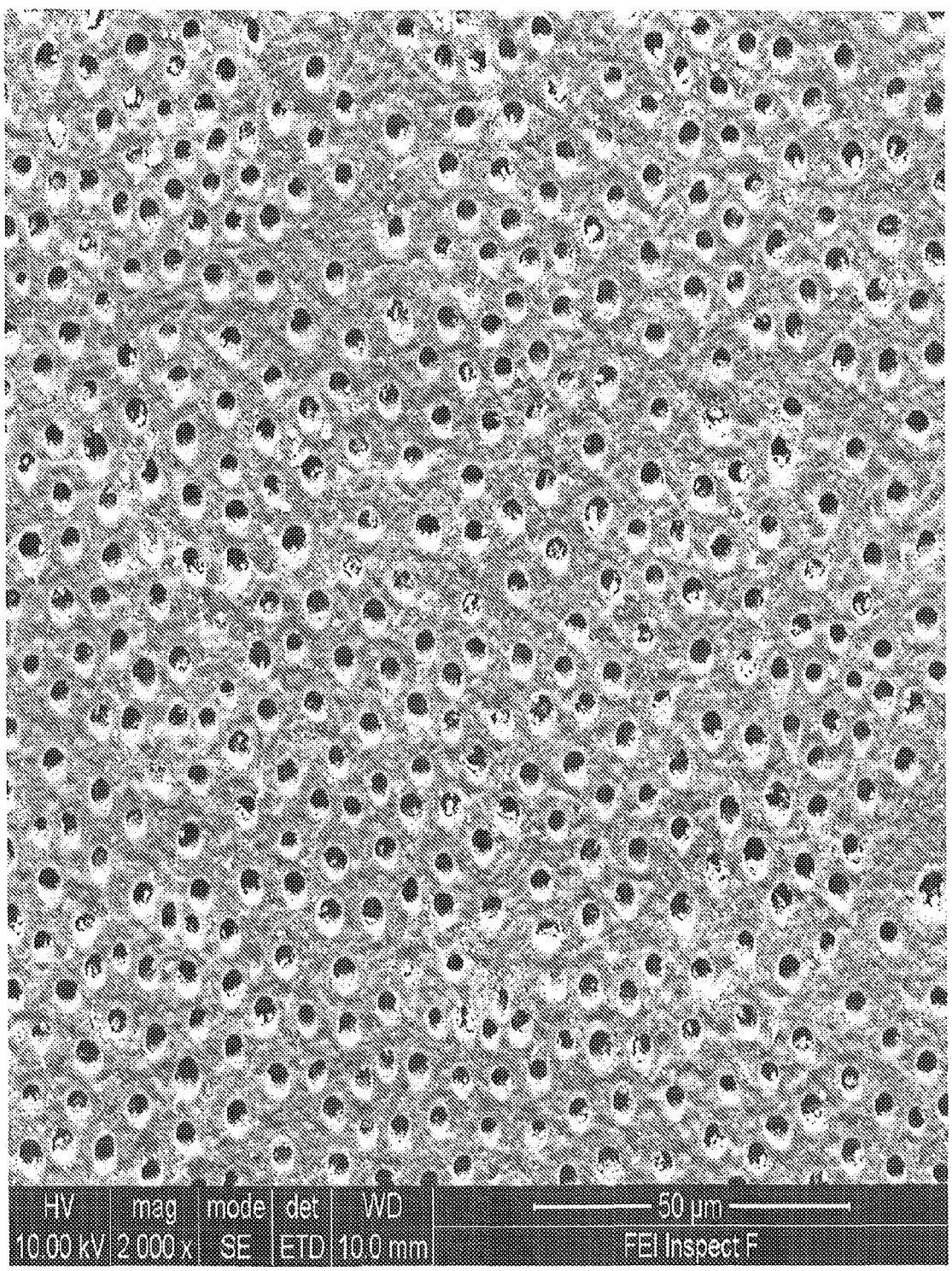
FIG. 3 shows a scanning electron micrograph of acid-etched dentine.
Figure 4:
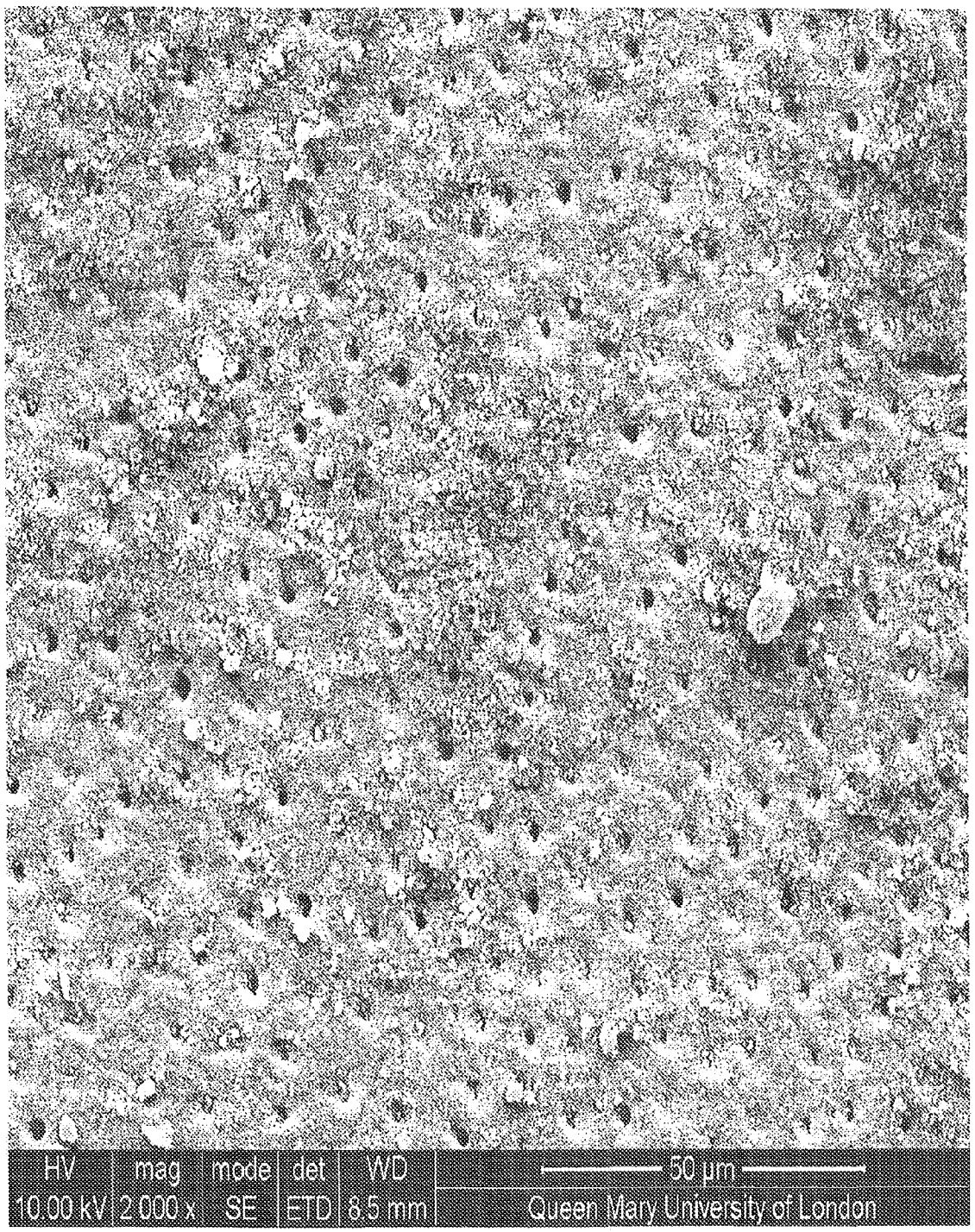
FIG. 4 shows a scanning electron micrograph of dentinal tubules following blocking with a composition according to the invention.

FIG. 3 shows a scanning electron micrograph of acid etched dentine, i.e. a molar tooth cut through the mid coronal section, which has been acid etched using 6% citric acid for 2 minutes. The tubules are clearly visible. The scanning electron micrograph in FIG. 4 shows these same tubules after a composition according to the invention comprising 7.5 wt % hydroxyapatite has been applied to the tooth. It can be seen that the dentinal tubules are substantially blocked by the particles in the composition, thus preventing the fluid flow through the dentinal tubules and minimising pain for the subject.

Figure 5:
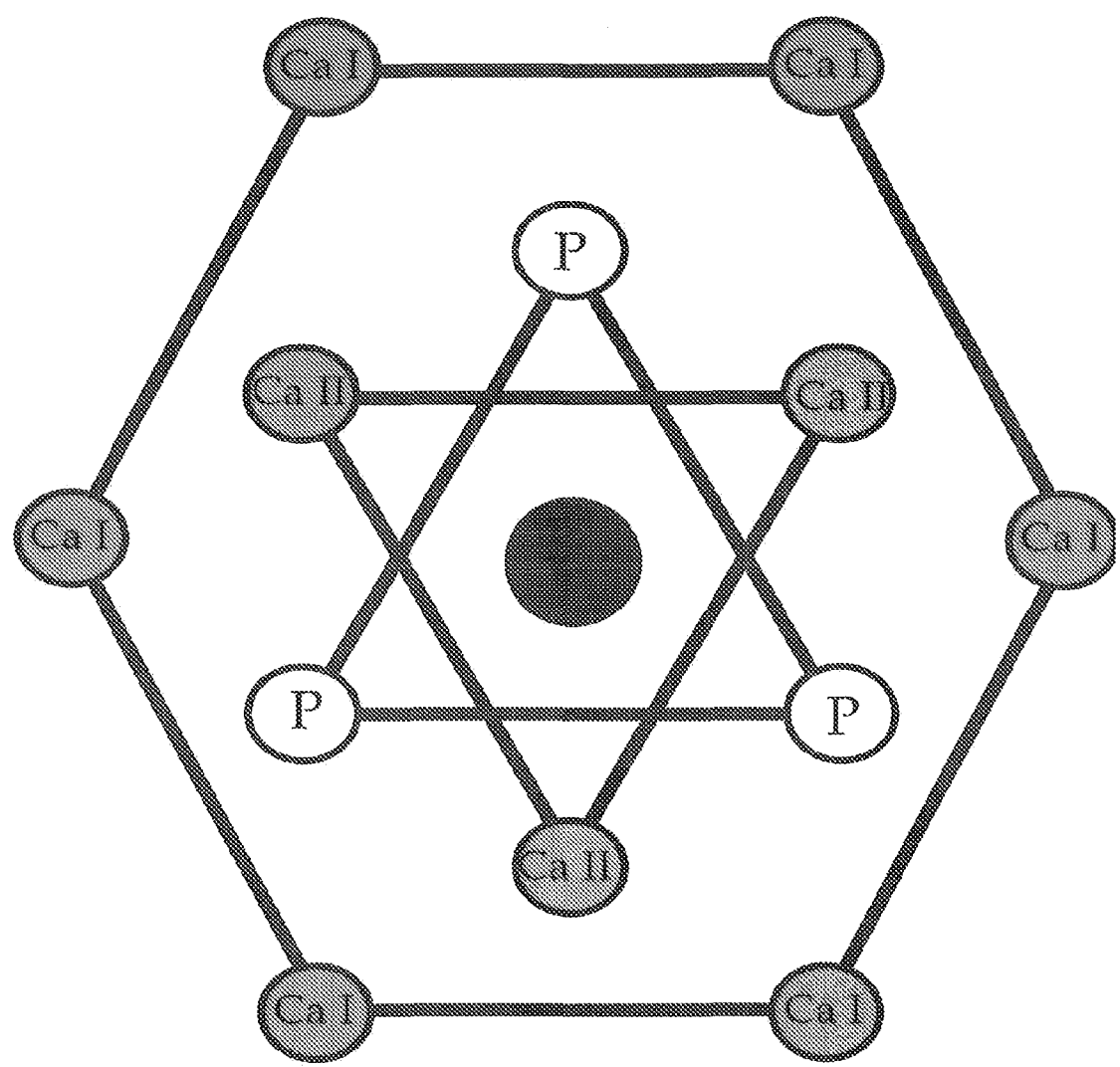
FIG. 5 shows the crystal structure of hydroxyapatite.

In FIG. 5, the crystal structure of hydroxyapatite, it can be seen that the smaller fluoride ion sits in the centre of the Ca(II) triangle, while the hydroxyl ion is displaced slightly above the plane of the triangle of Ca(II) ions.

Figure 6:
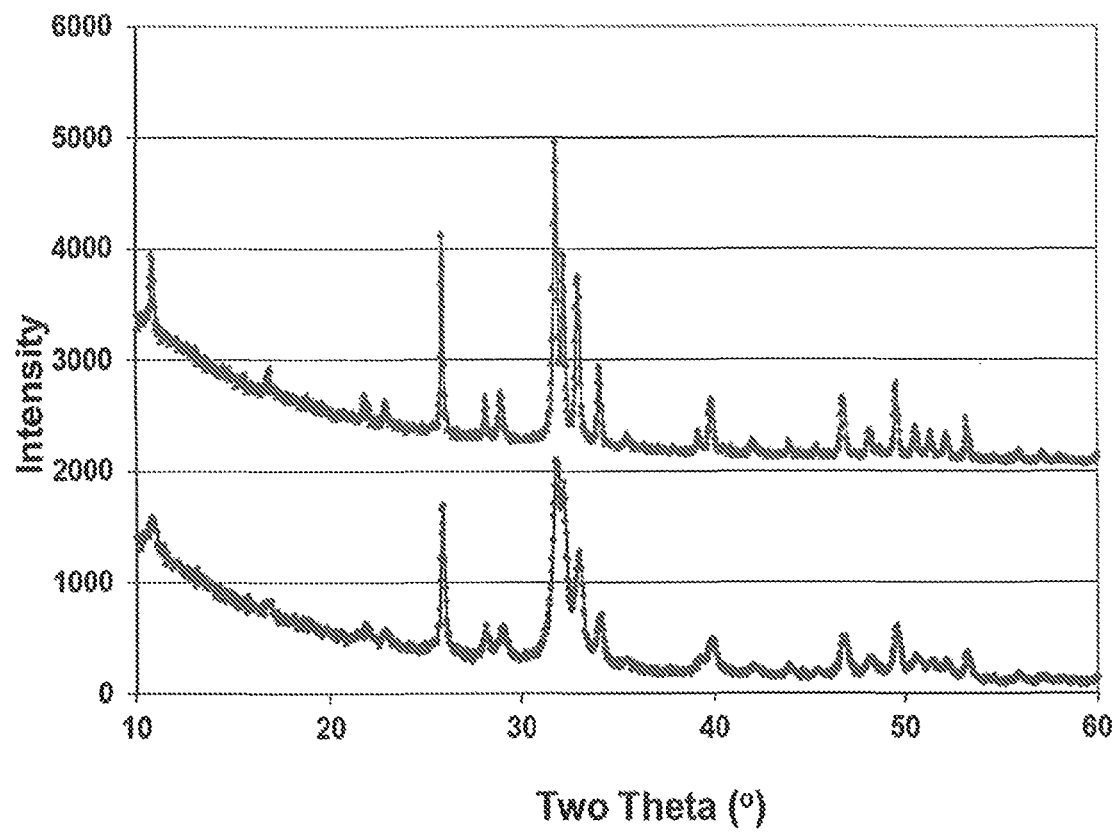
FIG. 6 shows X-ray powder diffraction patterns of a nano-crystalline hydroxyapatite (nHA) and of a micro-crystalline hydroxyapatite.

In FIG. 6, there is a comparison between the X-ray powder diffraction patterns of a nano-crystalline hydroxyapatite (nHA) and of a larger microcrystalline hydroxyapatite. It can be seen that the diffraction pattern of the nHA shows pronounced line broadening compared with that of the microcrystalline hydroxyapatite. Using Sherrer line broadening analysis, the nHCA has a crystallite size of 30 to 50 nm.

EXAMPLE 1

The method of manufacture of a typical toothpaste formulation according to the invention may be carried out in accordance with the following procedure:

To a vessel, purified water BP is added and stirring commences. Sodium saccharin, trisodium phosphate and sodium monofluorophosphate are added and allowed to dissolve. Glycerin and cellulose gum are premixed thoroughly and added to the main vessel using high shear mixing. Hydrated silica, hydroxyapatite and titanium dioxide are added and mixed under high shear until a smooth homogenous paste is created. The vessel has a jacket which is cooled with chilled water to ensure the contents remain below 40° C.

Menthol, peppermint oil BP & spearmint oil BP are pre-mixed in a separate vessel to create the flavour blend. This is subsequently added to the paste in the main vessel with mixing.

Chlorine dioxide 5% solution (proprietary blend) is added to the paste with mixing, and the pH of the paste is adjusted to comply with the specification using a citric acid/purified water BP premix and adequate stirring.

The final toothpaste formulation contains 1250 ppm of chlorine dioxide, 10900 ppm of sodium monofluorophosphate (which equates to 1428 ppm of fluoride in the monofluorophosphate, calculated by using the respective atomic and molecular weights of fluorine and sodium monofluorophosphate, which are 19 and 145, respectively), and 75000 ppm of hydroxyapatite.

EXAMPLE 2

The method of manufacture of a typical oral rinse or mouth wash formulation according to the invention may be carried out in accordance with the following procedure:

To a vessel, purified water BP/EP is added and is heated to 80° C. (±5° C.). The water is then stirred and recirculated through an in-line high shear homogeniser.

Kelcogel HA (high acyl content gellan gum—a polysaccharide consisting of glucose, rhamnose, and glucuronic acid repeat units and with a substituent glycerate moiety on every glucose unit and an acetate moiety on every second glucose moiety) and Cekol 4000 (a carboxymethyl cellulose polymer, used to minimise flocculation and aid bioadhesion) are pre-mixed in glycerol to wet-out. The glycerol containing the pre-mix is then added to the hot water. The resultant mixture is stirred and homogenised for 15 minutes before cooling.

When the temperature of the water reaches ≤65° C., sodium monofluorophosphate is then added to the vessel, followed by sodium citrate, tridsodium citrate and sodium saccharin. The introduction of $Na^+$ ions to the mixture causes the high acyl content gellan gum to thicken and form a fluid, highly mobile gel. The mixing and homogenising is continued.

When the temperature of the mixture in the vessel reaches ≤55° C., hydroxyapatite is added. The stirring and homogenising is continued until the mixture is fully dispersed and free from lumps. The homogeniser is then turned off and the mixture is stirred as it cools further.

In a separate vessel, a flavour pre-mix is prepared by adding polysorbate 20, PEG-60 hydrogenated castor oil, Frescolat MGA and Coolmint FL72627. These components are mixed thoroughly until a clear solution is obtained.

When the temperature of the mixture in the vessel reaches ≤40° C., sodium benzoate is added, and is allowed to fully dissolve with mixing. The flavour pre-mix is then also added to the main vessel, and the mixing continues.

When the temperature of the mixture in the vessel reaches ≤35° C., chlorine dioxide solution is added. The homogeniser is turned back on and the mixture is allowed to mix and homogenise for at least 15 minutes.

Citric acid is then added, and the mixture is allowed to mix for a further 15 minutes, to ensure that the pH of the product is 8.0-8.5. The homogenising and stirring then ceases, and the resultant product is protected from exposure to sunlight.

The final mouth wash or oral rinse formulation contains 1250 ppm of chlorine dioxide, 5000 ppm of sodium monofluorophosphate (which equates to 655 ppm of fluoride in the monofluorophosphate, again calculated by using the respective atomic and molecular weights of fluorine and sodium monofluorophosphate), and 50000 ppm of hydroxyapatite.

One of the key aspects of the present invention is the use of chlorine dioxide combined with the use of an apatite and fluoride. The chlorine dioxide role in the formulation is to remove plaque and biofilm from the tooth surface and particularly from exposed dentine surfaces; this serves to open the dentinal tubules and facilitates the subsequent occlusion of the dentinal tubules by the apatite particles. Conventionally, in laboratory studies of dentinal tubule, occlusion of mid coronal sections of human molars this is achieved using 6% citric acid or 35% orthophosphoric acid. Chlorine dioxide fulfils the same purpose within the toothpaste or oral rinse.

Figure 7A:
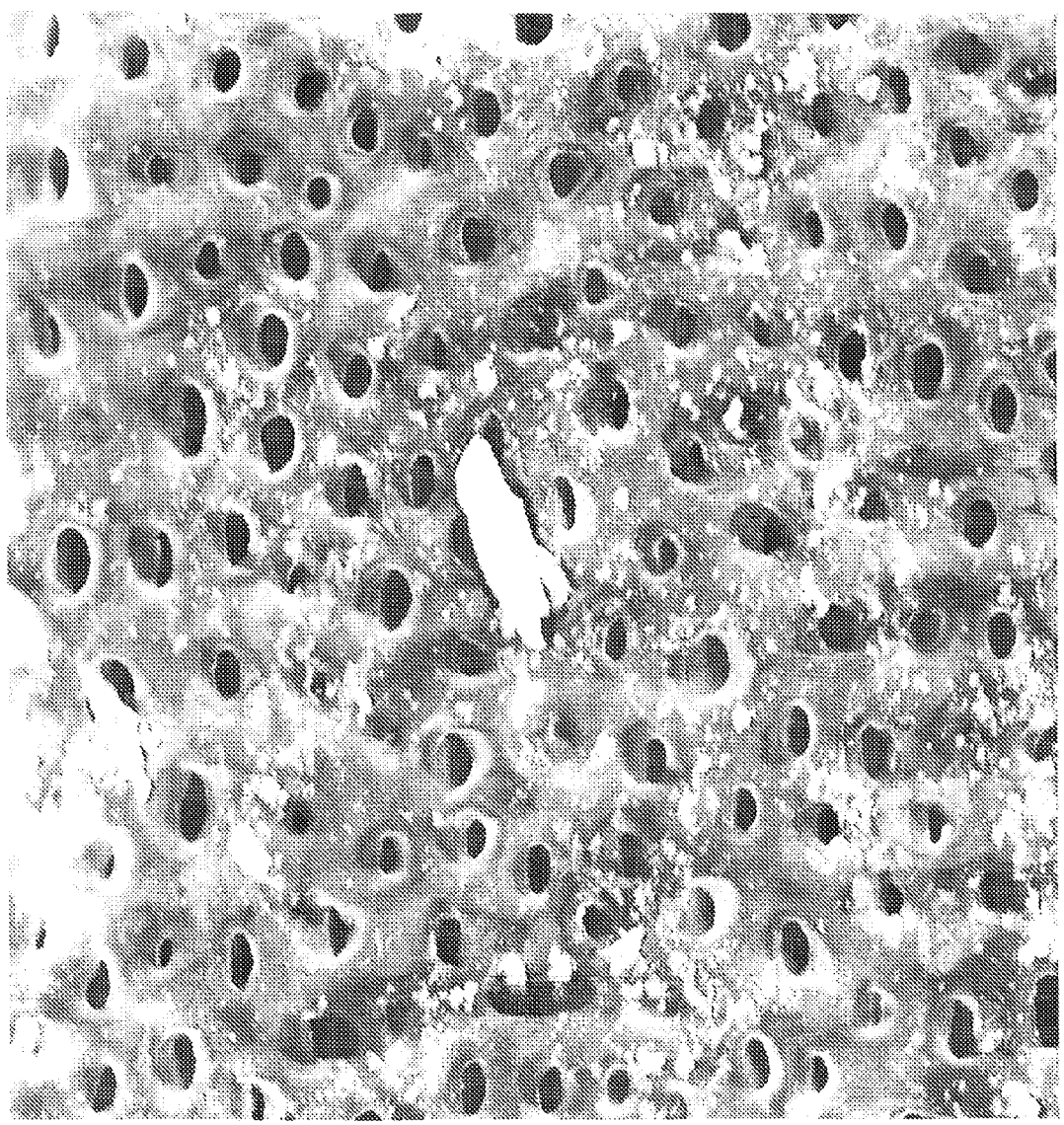
FIG. 7a shows an etched dentine surface of a mid-coronal section of a human molar.
Figure 7B:
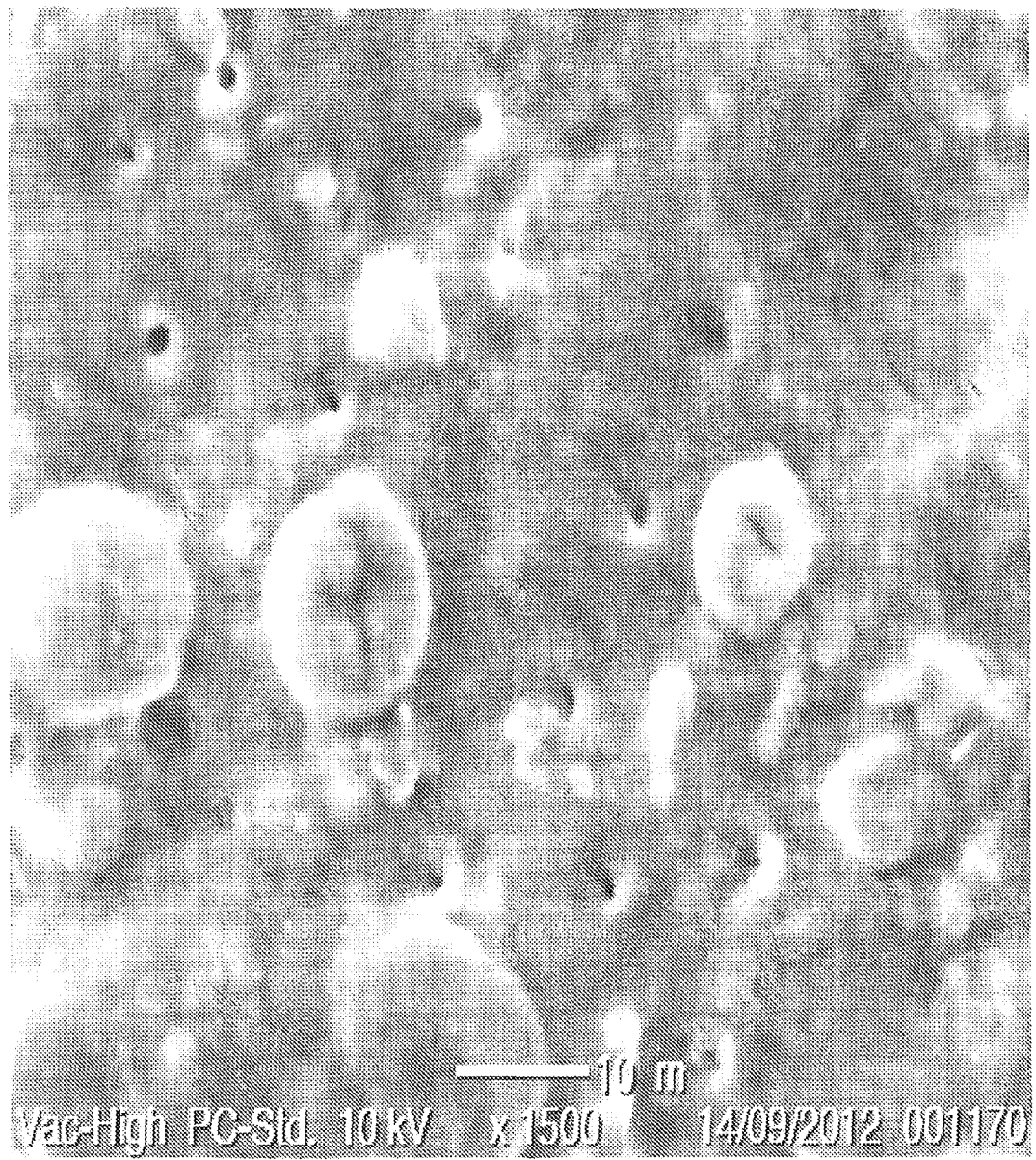
FIG. 7b shows a mucin-coated dentine surface to mimic biofilm.
Figure 7C:
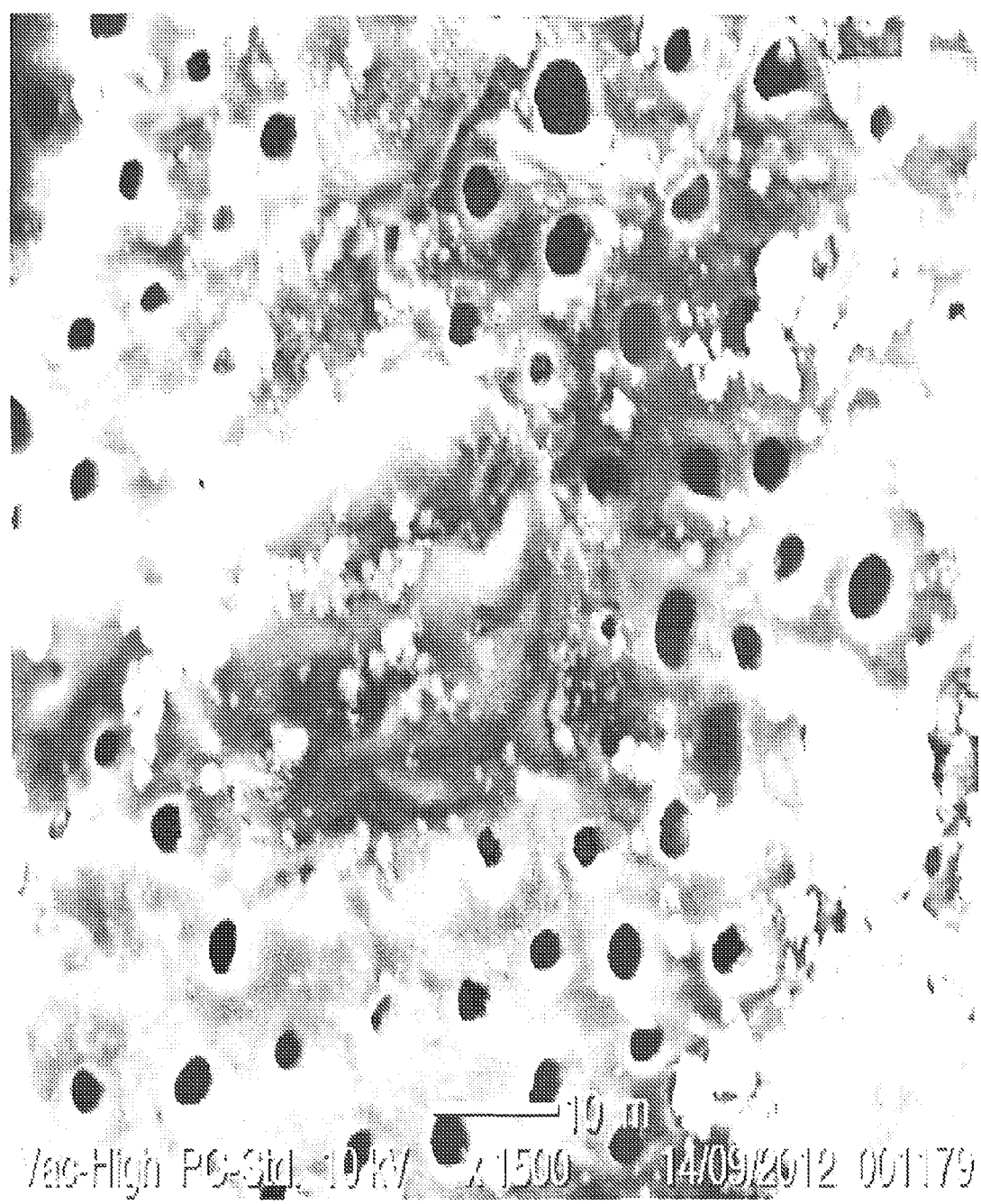
FIG. 7c shows a tooth surface after treatment with a chlorine dioxide toothpaste according to the invention, but containing silica powder instead of hydroxyapatite.

FIG. 7a shows an SEM of a mid-coronal section of a human molar treated with 6% citric acid for 2 minutes to open the dentinal tubules then painted with a 2.5% solution of mucin, a common salivary protein, air dried and then followed by a stabilisation treatment with 10% formalin solution. The process was repeated to produce a water stable protein biofilm. It can be seen (FIG. 7b) that following treatment the tubules are occluded with the biofilm. A toothpaste based on Table 2, but where the occluding agent in the formulation, hydroxyapatite, is replaced by silica powder was then applied to the tooth surface for 2 minutes, followed by rinsing with distilled water. It can be seen (FIG. 7c) that the chlorine dioxide in the toothpaste breaks down the protein layer and opens the dentinal tubules. However, it must also be noted that the silica added to replace the hydroxyapatite in the toothpaste acts in a negative manner to partially occlude some of the dentinal tubules. Application of formulations without the chlorine dioxide failed to result in opening of the dentinal tubules.

One of the key aspects of the invention is the ability of the apatite to work in conjunction with a source of fluoride to promote remineralisation. This is particularly important with regard to replacing lost tooth mineral due to acid erosion, incipient caries, or to promote the conversion of the apatite occluding the dentinal tubules to more durable fluoridated apatite. This is illustrated by two techniques:

i) Surface micro-hardness measurements, since an increase in mineral content results in an increase in hardness; or
ii) Direct evidence of the formation of the formation of fluoridated apatite using $^{19}F$ solid state nuclear magnetic resonance spectroscopy using enamel slices and associated weight changes and fluoride measurements.

Quantification of the Enamel Remineralisation by Microhardness Test

Studies were carried out according to the following experiment protocol. Fifteen human molars were collected, disinfected, embedded in resin, polished down to reveal longitudinal section and finished with 1 micron diamond paste. Enamel hardness was evaluated using a microhardness tester (Duramin-1/-2; Struers, Copenhagen, Denmark) with a Vicker's indenter (a square pyramid diamond shape indenter) under a load of 50 g for 15 seconds. 10 indentations per sample were taken. The two diagonal indentation lengths were measured and then used for microhardness calculation using the following equation:

$$HV = \frac{F}{A}$$
$$\approx \frac{1.8544F}{d^2}$$

where F is in kilogram-force (kgf), A is the area of the point of the indenter, and d is the average length of the diagonal left by the indenter in millimeters.

The teeth specimens were demineralised in a demineralisation solution (pH=4.5, 50 mM acetic acid to mimic an acidic challenge during a caries attack) and the hardness was then again measured.

Figure 8:
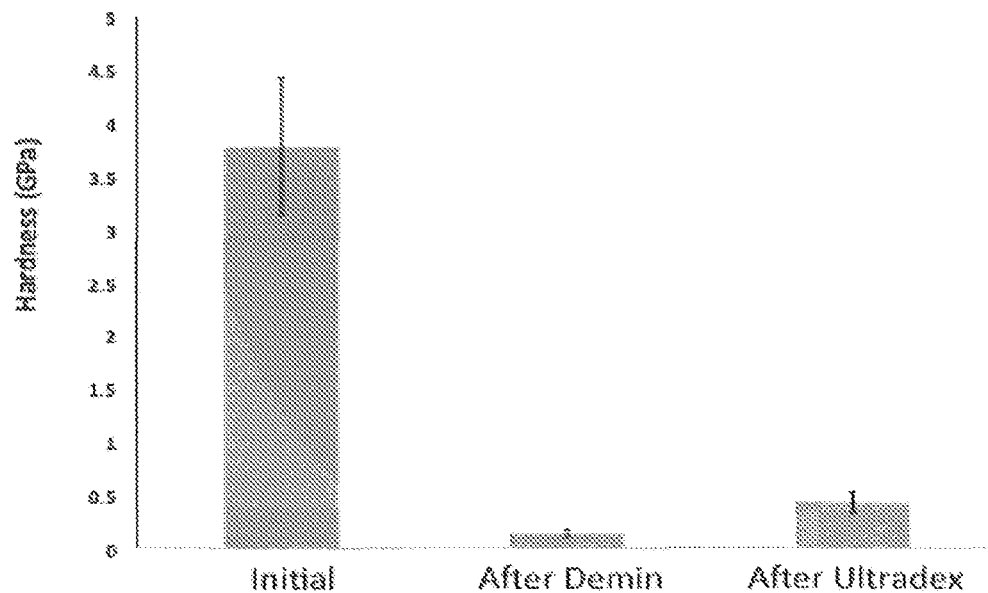
FIG. 8 shows the hardness values of the tooth surface of the molars after applying a toothpaste according to the invention.

The toothpaste of the invention was then applied to the tooth surface and the hardness again measured. FIG. 8 shows the hardness values. Following the acid challenge the hardness decreases significantly, but increases significantly after exposure to the toothpaste providing clear evidence of remineralisation.

$^{19}F$ MAS-NMR Study of the Fluorapatite Formation

Caries-free first molar and premolars were collected and stored in 3% sodium hypochlorite solution for 24 hours. Teeth were mounted in acrylic resin, and sliced using an annular diamond blade (Microslice 2, Malvern Instrument, UK) to get enamel sections (approximately 6×5×1 mm$^3$). Excess dentine area was removed by polishing against P600 silicon carbide paper.

The enamel blocks were then rinsed off with de-ionized water, dried in air for 30 minutes and weighed using a digital microbalance. Each enamel section was immersed in 50 ml acetic acid solution (0.1 M, pH=4.0) and agitated at a rate of 60 rpm in a 37° C. incubator (KS 4000 I control, IKA) for 24 hours. The enamel specimens were then immersed in the toothpaste according to the invention, Ultradex Toothpaste (diluted 1:10 with acetic acid solution (pH=4.0) to give a 0.1M final solution, to mimic the real mouth situation), or in the mouth wash according to the invention, Ultradex Recalcifying and Whitening Oral Rinse treatment solution (diluted 1:2 both with 0.2 M acetic acid solution (pH=4.0) to mimic the real mouth situation), placed back in the incubator, and agitated at a rate of 60 rpm for 96 hours. After treatment, the enamel blocks were cleaned, dried and weighed. The enamel weight loss was presented in percentages. Enamel samples (no treatment, 24 hours demineralised and demineralization followed by the treatments) were ground to powder using a vibratory mill (MM200, Glen Creston Ltd, UK) with a 25 ml zirconia grinding jar for 15 seconds under 20 Hz. The powder was then used for solid-state NMR experiments using the 600 MHz (14.1 T) Bruker spectrometer. The $^{19}$F solid state NMR measurements were run at the resonance frequency of 564.7 MHz with a 2.5 mm rotor spun at 18 and 21 kHz. Spectra were obtained by overnight scans with 8 preliminary dummy scans and 60 seconds recycling delay. The chemical shift was referenced using the signal from the 1M NaF solution scaled to −120 ppm relative to the $CF_3Cl$ primary standard.

Figure 9:
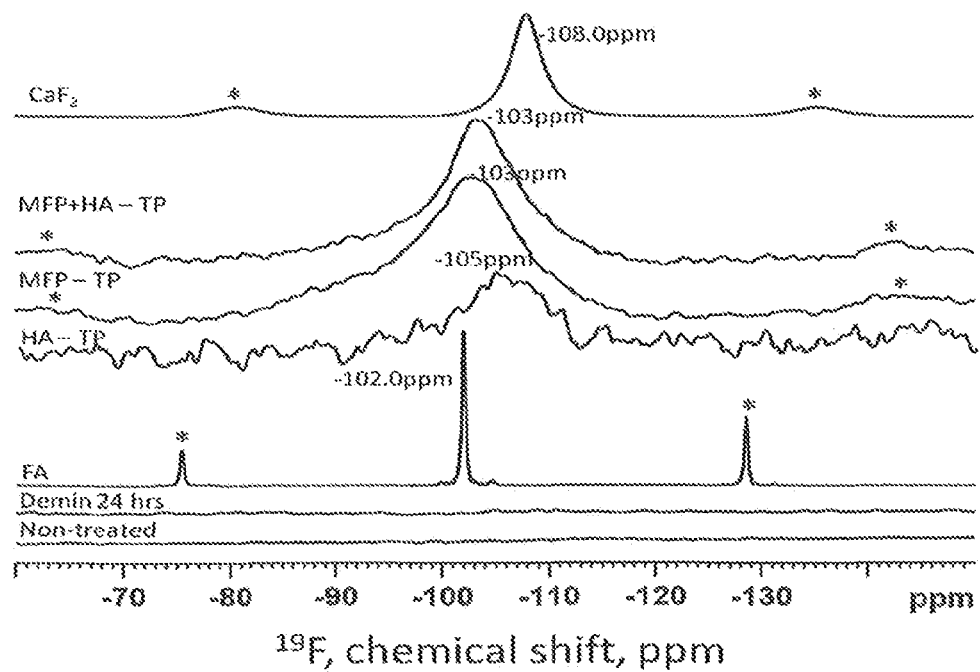
FIG. 9 shows NMR spectra for enamel samples; non-treated, demineralised and treated with a toothpaste according to the invention.
Figure 10:
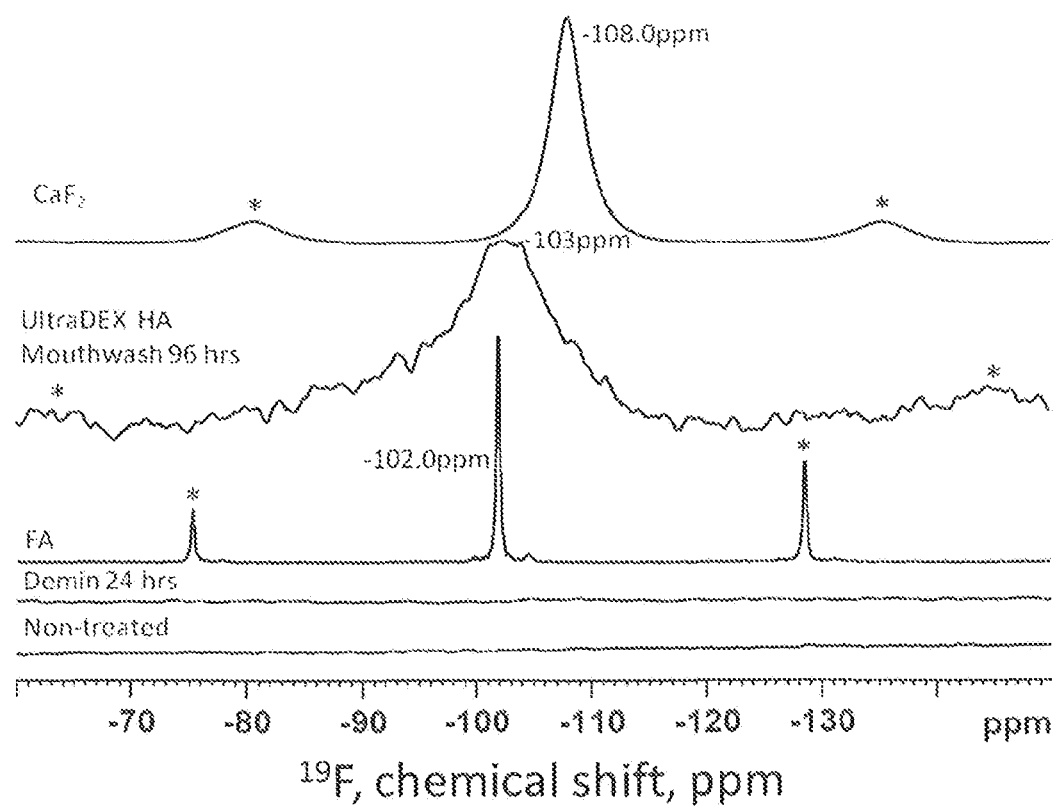
FIG. 10 shows NMR spectra for enamel samples non-treated, demineralised and treated with a mouth wash according to the invention.

The NMR spectra showed flat lines for both the non-treated enamel sample and the demineralised enamel sample (FIGS. 9 and 10). Therefore, there was no fluoride detected for both samples. This indicated that no significant fluoride was present in the original tooth samples. The spectra were then run for the toothpaste and oral rinse samples. The toothpaste with both HA and monofluorophosphate (MFP) showed the presence of fluorapatite with a chemical shift of −103 ppm, the position being almost identical to the chemical shift of the fluorine in fluorapatite (−102 ppm), as did the toothpaste with MFP alone treated samples. The HA toothpaste alone gave a very small signal close to that of fluorite, which was probably present in the original tooth. The oral rinse treated enamel sample showed a broad peak centered at around −103 ppm, This demonstrates that after demineralisation treatment, the Ultradex Recalcifying and Whitening Toothpaste and Oral Rinse treatment of the invention led to fluorapatite formation. The reference spectrum for the fluorapatite was based on synthetic pure fluorapatite, which demonstrates a distinct sharp peak with a chemical shift at −102 ppm. The apatite that comprises the tooth enamel is a solid solution formed rather than stoichiometric. It could contain different ions such as Magnesium ($Mg^{2+}$) and Manganese ($Mn^{2+}$) substituted for $Ca^{2+}$, fluoride ($F^-$) substituted for hydroxyl ($OH^-$), and carbonate ($CO_3^{2-}$) substituted for phosphate ($PO_4^{3-}$). The crystal structure is therefore distorted. With demineralisation and subsequent remineralisation, the fluorapatite crystals formed could therefore be slightly disordered. This may explain why the spectrum for the Ultradex Recalcifying and Whitening Toothpaste and Oral Rinse of the invention treated enamel showed broader peaks when compared with the fluorapatite reference. Fluoride promotes remineralisation and the fluorapatite formed is more acid resistant compared with the hydroxyapatite and carbonated hydroxyapatite. However, high concentrations of fluoride with insufficient phosphate ions may result in the formation of the undesirable calcium fluoride phase.

Figure 11:
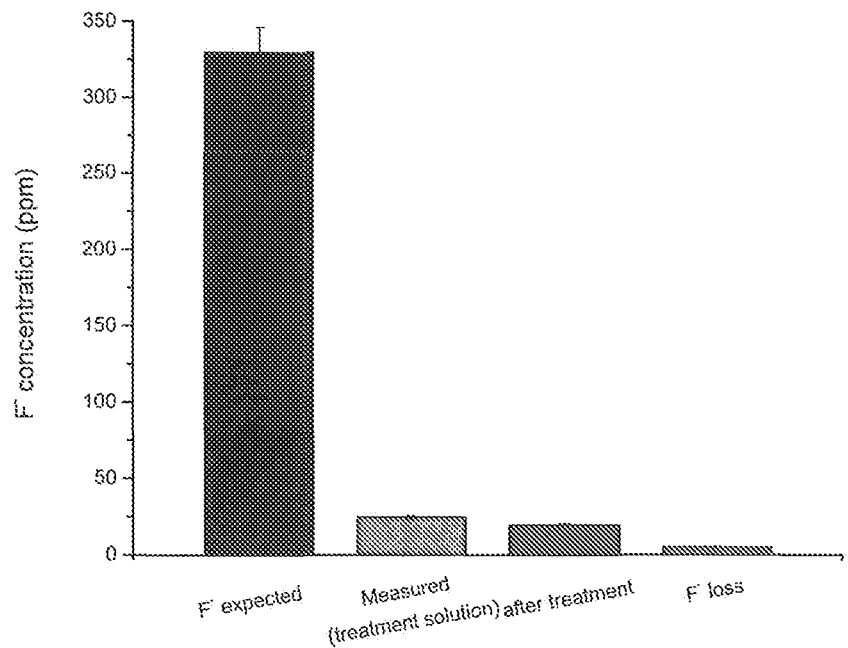
FIG. 11 shows a graph illustrating the amount of total fluoride in a mouth wash according to the invention in relation to the amount of active, or free, fluoride available for remineralisation.

An Ultradex Recalcifying and Whitening Oral Rinse/mouth wash of the invention contains 660 ppm in the form of monofluorophosphate, with a 1:2 dilution, the total available $F^-$ was 330 ppm. However, the actual available $F^-$ detected by a fluoride selective electrode (ORION 9609BN PH/ISE meter model 710 A, USA) (FIG. 11) was only 24.5 ppm. The $F^-$ after the remineralisation was 19.5 and this gave an $F^-$ loss of 5 ppm. This further confirms fluoride is being incorporated into the apatite.

Figure 12:
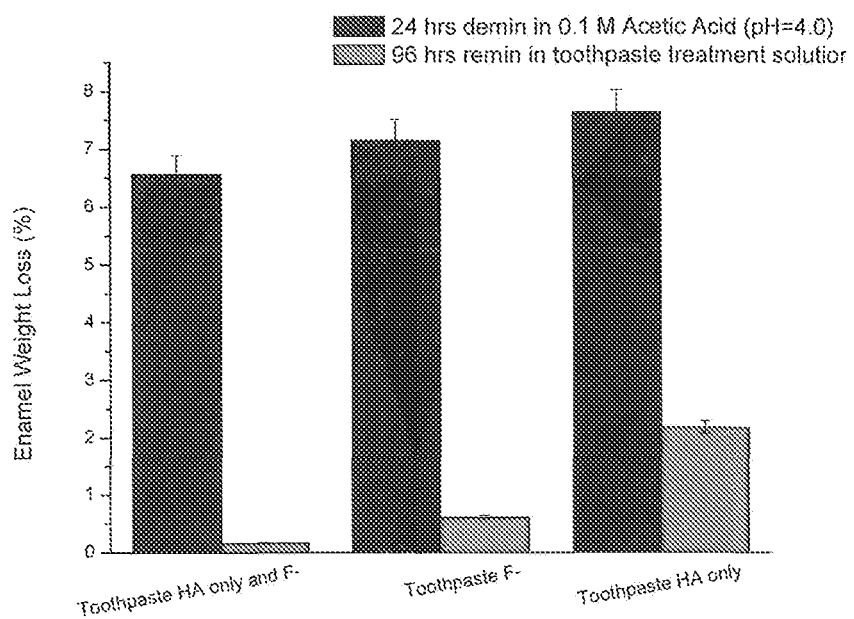
FIG. 12 shows a graph illustrating the enamel weight loss during the demineralisation and treatment with a toothpaste according to the invention.

The weight loss of the sample toothpaste specimens are given in FIG. 12. Both MFP and HA acted to reduce weight loss and enamel demineralisation. However the biggest reduction in weight loss was found for the Ultradex Recalcifying Whitening Oral Toothpaste treatment (i.e. the composition of Table 2). This indicates that the fluoride acts synergistically with the HA to inhibit demineralisation and promote remineralisation.

Figure 13:
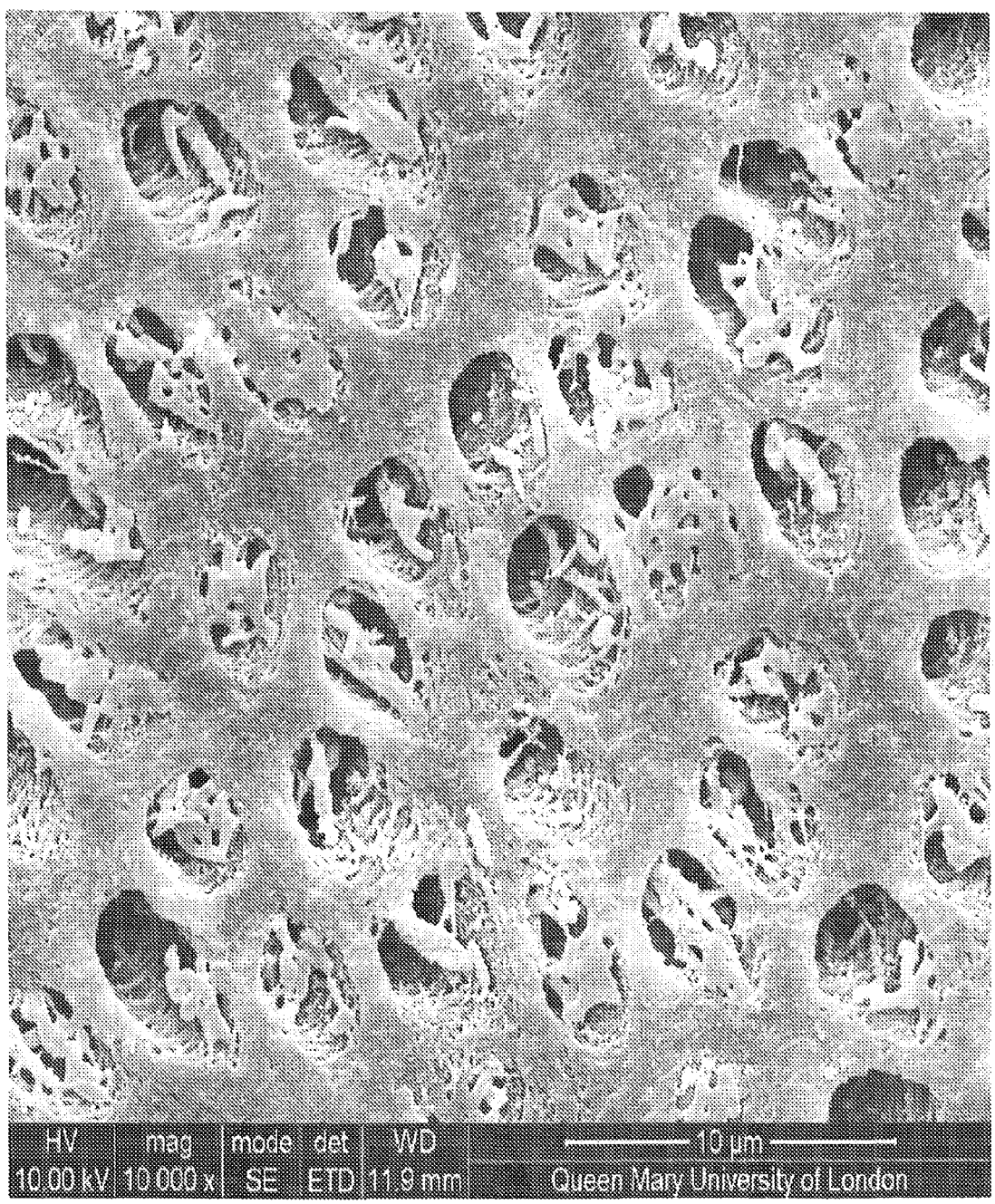
FIG. 13 shows a scanning electron micrograph of a dentine surface of a specimen treated for 1 day with a mouth wash according to the invention (4×2 minutes of treatment, followed by remineralisation).

Further, the scanning electron micrograph in FIG. 13 clearly demonstrates that a tooth specimen that is treated over a period using the mouth wash of the invention—in this case over 1 day, with 4 lots of 2 minutes' worth of treatment with the mouth wash, followed by the remineralisation—achieves the aim of successfully occluding the dentinal tubules, and thus reduce dentine hypersensitivity.

Figure 14:
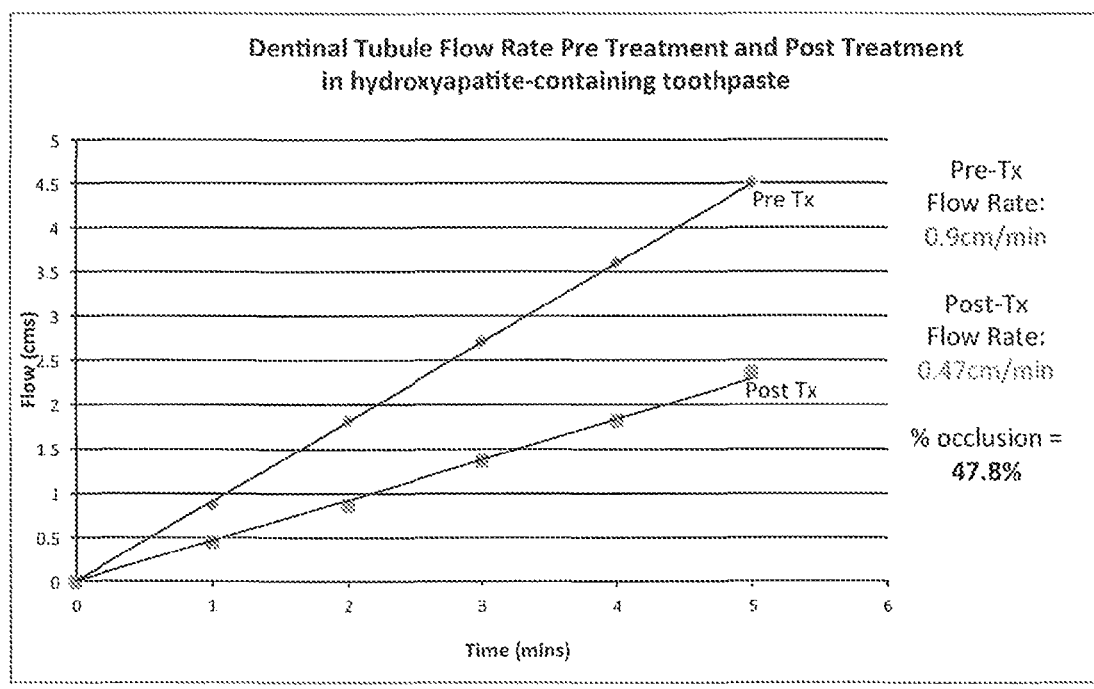
FIG. 14 shows a graph illustrating reduction in fluid flow through dentinal tubules following tooth brushing with a toothpaste according to the invention.

In FIG. 14, it can be seen from the graph that there is a reduction in fluid flow through dentinal tubules following tooth brushing with a toothpaste according to the invention, thus indicating that the tubules have been successfully blocked by the action of the fluoride in the remineralisation process. This is a test that is routinely used as a measure of the efficacy of a hypersensitivity toothpaste.

Therefore, in summary, it can be seen that the composition of the invention provides technical advantages over existing formulations lacking any one of the defined components. Application to the surface of teeth of formulations containing no chlorine dioxide results in a failure to break down the biofilm and open up the dentinal tubules to be filled, as illustrated in relation to FIG. 7c above. Application of formulations containing no hydroxyapatite (i.e. a source of both calcium and phosphate ions) and using another component instead results in the opened tubules being undesirably partially occluded, thus hindering their refilling during the remineralisation process, and thus hindering the treatment of dentine hypersensitivity. Finally, it is clear that formulations lacking any fluoride ion source would not be able to provide any remineralisation of the tooth at all.

It is of course to be understood that the present invention is not intended to be restricted to the foregoing examples which are described by way of example only.

The invention claimed is:

1. An oral care composition comprising:
   i) a source of a fluoride ion;
   ii) a source of a calcium ion;
   iii) a source of a phosphate ion; and
   iv) stabilized chlorine dioxide,
   wherein the source of the calcium ion and the source of the phosphate ion comprises a particulate apatite species, and wherein the pH of the composition is between about 6.0 and about 8.0.

2. The oral care composition according to claim 1, wherein the particulate apatite species comprises apatite particles, wherein the apatite particles comprise crystallites having a size of less than about 100 nm.

3. The oral care composition according to claim 2, wherein the apatite species is based on the formula $M_5(PO_4)_{3}X$, wherein M is Ca, Sr, Zn or Mg, and X is F, Cl or OH.

4. The oral care composition according to claim 2, wherein the apatite species is a substituted or unsubstituted hydroxyapatite or a substituted or unsubstituted fluorapatite.

5. The oral care composition according to claim 2, wherein the apatite species is selected from calcium hydroxyapatite, strontium hydroxyapatite, calcium hydroxycarbonated apatite, strontium hydroxycarbonated apatite, calcium fluorapatite, strontium fluorapatite, mixed strontium calcium apatites or a mixed hydroxyfluorapatite, zinc substituted hydroxyapatite, zinc carbonated hydroxyapatite, zinc fluorapatite, octacalcium phosphate, or a mixture of any two or more thereof.

6. The oral care composition according to claim 2, wherein the apatite species is present in an amount of from about 0.5 to about 25 weight percent of the composition, and/or the apatite species has a particle size distribution.

7. The oral care composition according to claim 1, wherein the source of a fluoride ion is selected from sodium fluoride, potassium fluoride, disodium monofluorophosphate, tin(II) fluoride, dipotassium fluorophosphates, calcium fluorophosphates, calcium fluoride, ammonium fluoride, aluminium fluoride, hexadecyl ammonium fluoride, 3-(N-hexadecyl-N-2-hydroxy-ethylammonio) ammonium difluoride, N,N'

N'-tris(polyoxyethylene)-N-hexadecylpropylenediaminedihydrofluoride disodium hexafluorosilicate, dipotassiumhexafluorosilicate, ammonium hexafluorosilicate, magnesium hexafluorosilicate or ammonium fluorophosphates, or any combinations of two or more thereof.

8. The oral care composition according to claim 1, wherein the source of fluoride ion provides a fluoride concentration in the composition of between 20 and 1500 ppm.

9. The oral care composition according to claim 8, wherein when the composition is to be used as toothpaste, the fluoride concentration is between 300 and 1500 ppm.

10. The oral care composition according to claim 8, wherein when the composition is to be used as mouth wash, the composition has an active fluoride concentration between 5 and 500 ppm.

11. The oral care composition according to claim 1, further comprising a buffer system.

12. The oral care composition according to claim 11, wherein the buffer system comprises one or more selected from acetate, carbonate, citrate or phosphate-containing species.

13. The oral care composition according to claim 1, wherein when the composition is a mouth wash or oral rinse, it further comprises a linear polysaccharide polymer.

14. The oral care composition according to claim 13, wherein the linear polysaccharide polymer is a linear polysaccharide gum, wherein one or more hydroxyl groups on a monosaccharide of the linear polysaccharide gum is substituted with a functional group comprising a group selected from a carboxyl group (R—COOH), an acyl group (RCO—) or a sulphate group (R—$OSO_3^-$).

15. An oral care composition according to claim 1, wherein the oral care composition is in the form of a toothpaste, oral spray, mouthwash or oral rinse formulation.

16. A method for generating gaseous chlorine dioxide within an oral cavity of a subject for a medical purpose comprising, combining stabilized chlorine dioxide solution, an apatite species, and a source of a fluoride ion.

17. The method according to claim 16, wherein the stabilized chlorine dioxide solution has a concentration of between about 0.05% to about 2.0% (w/v).

18. The method according to claim 16, wherein the medical purpose is cleaning teeth and mucous membranes, perfuming teeth and mucous membranes, protecting teeth and mucous membranes, change the appearance of teeth and mucous membranes, correct unpleasant odours, remineralization of teeth, dentine hypersensitivity, and a combination of medical purposes.

19. A method of cleaning teeth and mucous membranes of an oral cavity of a subject, or perfuming them or protecting them, comprising applying an oral care composition according to claim 1.

20. The oral care composition according to claim 2, wherein the apatite particles have a size distribution such that at least 50% by mass of the apatite particles have a size of less than about 5 microns.

21. The oral care composition according to claim 1, wherein the crystallites of the particulate apatite species are of a size of from about 30 nm to about 50 nm, and wherein the apatite particles have a particle size distribution such that at least 15% of the mass of the apatite particles have a size of less than about 5 microns.

22. The oral care composition according to claim 15, wherein the oral care composition is in the form of a toothpaste, and wherein the apatite species is a nanocrystalline hydroxyapatite, and wherein the apatite particles form approximately spherical particles with dimensions of from 0.1 to 5 microns.

* * * * *